(12) United States Patent  
Blankenstein et al.

(10) Patent No.: US 7,318,359 B2  
(45) Date of Patent: Jan. 15, 2008

(54) SAMPLING MEANS AND SYSTEM FOR TESTING A SAMPLE LIQUID

(75) Inventors: Gert Blankenstein, Dortmund (DE); Thomas Willms, Castrop-Rauxel (DE)

(73) Assignee: Boehringer Ingelheim microParts GmbH, Dortmund (DE)

( * ) Notice: Subject to any disclaimer, the term of this patent is extended or adjusted under 35 U.S.C. 154(b) by 506 days.

(21) Appl. No.: 11/008,573

(22) Filed: Dec. 10, 2004

(65) Prior Publication Data

US 2005/0145046 A1 Jul. 7, 2005

(30) Foreign Application Priority Data

Dec. 12, 2003 (DE) ................. 103 58 775

(51) Int. Cl.  
*G01N 1/00* (2006.01)
(52) U.S. Cl. ................ 73/864.22; 73/864.21
(58) Field of Classification Search ........... 73/64.56, 73/864.22, 864.21, 864.73; 422/68.1, 100; 435/309.1; 436/74; 600/576

See application file for complete search history.

(56) References Cited

U.S. PATENT DOCUMENTS

| 3,453,941 A | | 7/1969 | Marachy |
| 3,869,068 A | | 3/1975 | Chen |
| 4,589,421 A | | 5/1986 | Ullman |
| 4,978,504 A | * | 12/1990 | Nason .................... 422/61 |
| 5,266,266 A | * | 11/1993 | Nason .................... 422/58 |
| 5,726,026 A | * | 3/1998 | Wilding et al. ........ 435/7.21 |
| 6,039,488 A | * | 3/2000 | Krawczyk et al. ...... 401/132 |
| 6,383,804 B1 | * | 5/2002 | Ward et al. ............ 435/309.1 |
| 6,656,431 B2 | * | 12/2003 | Holl et al. .............. 422/68.1 |

FOREIGN PATENT DOCUMENTS

| DE | 33 024 A1 | 3/1987 |
| JP | 59-15835 | 1/1984 |

* cited by examiner

*Primary Examiner*—Robert Raevis  
(74) *Attorney, Agent, or Firm*—David S. Safran (57) ABSTRACT

A sampling device and a system for testing of sample liquid are proposed. Very simple and prompt testing of the sample liquid is enabled in that the sampling device has a reservoir for the dilution liquid and that the taken-up sample liquid can be delivered by the dilution liquid directly to the testing area.

64 Claims, 8 Drawing Sheets

SAMPLING MEANS AND SYSTEM FOR TESTING A SAMPLE LIQUID

BACKGROUND OF THE INVENTION

1. Field of Invention

This invention relates to a sampling means for taking up sample liquid, especially blood, saliva, or other fluid of the human or an animal body, and for delivery, especially to a testing means, with a take-up means for the sample liquid, and a system for testing the sample liquid with the sampling means.

2. Description of Related Art

To test a sample liquid, especially blood, saliva, or other fluid of the human or an animal body, the following is known from practice: taking-up a sample liquid, for example, blood, from a finger by means of a capillary, then inserting the capillary with the sample liquid into a vessel with a dilution liquid, conventionally, shaking being necessary for mixing of the sample liquid with the dilution liquid and for dilution. Then, the sample liquid can be tested, but the diluted sample liquid in an additional step having to be supplied first to an analysis means. Testing the sample liquid is accordingly relatively complex and time-consuming.

SUMMARY OF THE INVENTION

A primary object of this invention is to devise a sampling means for take-up and delivery of sample liquid and a system for testing a sample liquid so that the sample liquid can be tested easily and preferably very promptly.

The aforementioned object is achieved by a sampling means that has an integrated reservoir for the dilution liquid and is made portable and by the sample liquid and the dilution liquid being delivered in succession or at the same time by means of a manually actuated pump means.

The object is also achieved by a system for testing a sample liquid in which the sampling means of the present invention is combined with a means for taking up the sample liquid and a means for testing it.

The underlying idea of the invention is to provide the sampling means with a reservoir for a dilution liquid and/or reaction liquid, and the sample liquid and the dilution liquid and/or reaction liquid can be delivered in succession or at the same time, especially by a single actuation of the sampling means. In particular, the sample liquid is washed out or flushed out by the stored dilution and/or reaction liquid, and at the same time, is mixed and diluted with the dilution and/or reaction liquid when taken up into the take-up chamber. This enables very simple handling with only one step or few steps and allows prompt sampling and subsequent testing since a separate intermediate step of mixing and diluting is eliminated.

Another advantage of the approach in accordance with the invention is that a separate container for the dilution and reaction liquid is not necessary. Rather the sampling means with the integrated reservoir for the dilution liquid and a testing means are sufficient to form a fully serviceable, preferably transportable or portable system for testing of sample liquids.

Simply, the expression "dilution liquid" is used below for the further description and in the claims for the sake of simplification, but term is intend to include liquids which, in particular, can also contain especially reagents which can react with components of the sample liquid. The "dilution liquid" as used herein is, therefore, a liquid which can cause dilution, buffering and/or reaction or the like with the sample liquid.

Other advantages, features, properties and aspects of this invention will be apparent from the following description of preferred embodiments with reference to the accompanying drawings.

DETAILED DESCRIPTION OF THE INVENTION

In the figures, the same reference numbers are used for the same or similar parts, the corresponding or comparable properties and advantages being achieved even if a repeated description is omitted.

Figure 1:
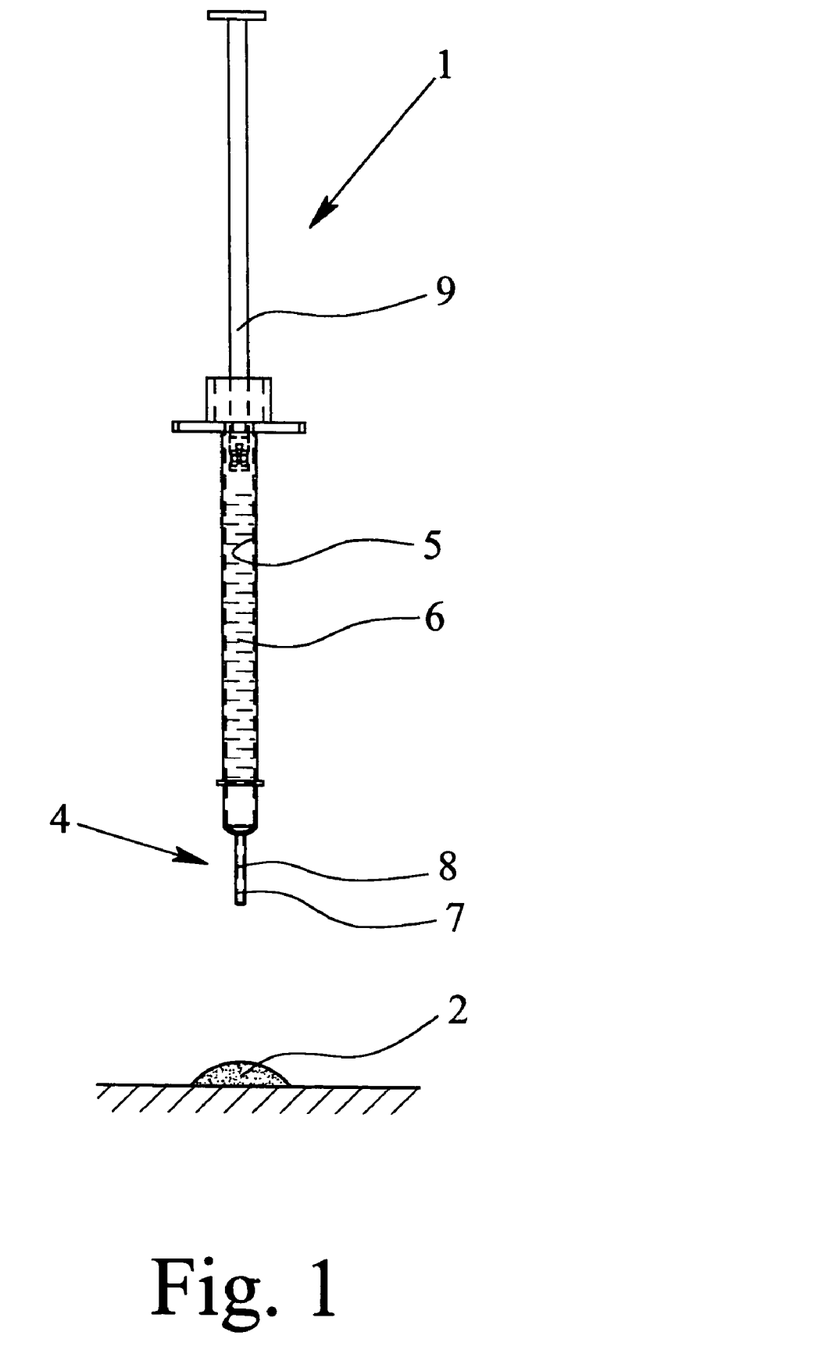
FIG. 1 is a schematic representation of a sampling means in accordance with a first embodiment of the invention before taking up the sample liquid.

FIG. 1 schematically shows a first embodiment of a sampling means 1 in accordance with the invention for taking up sample liquid 2, especially blood, saliva, or other fluid of the human or an animal body.

Figure 4:
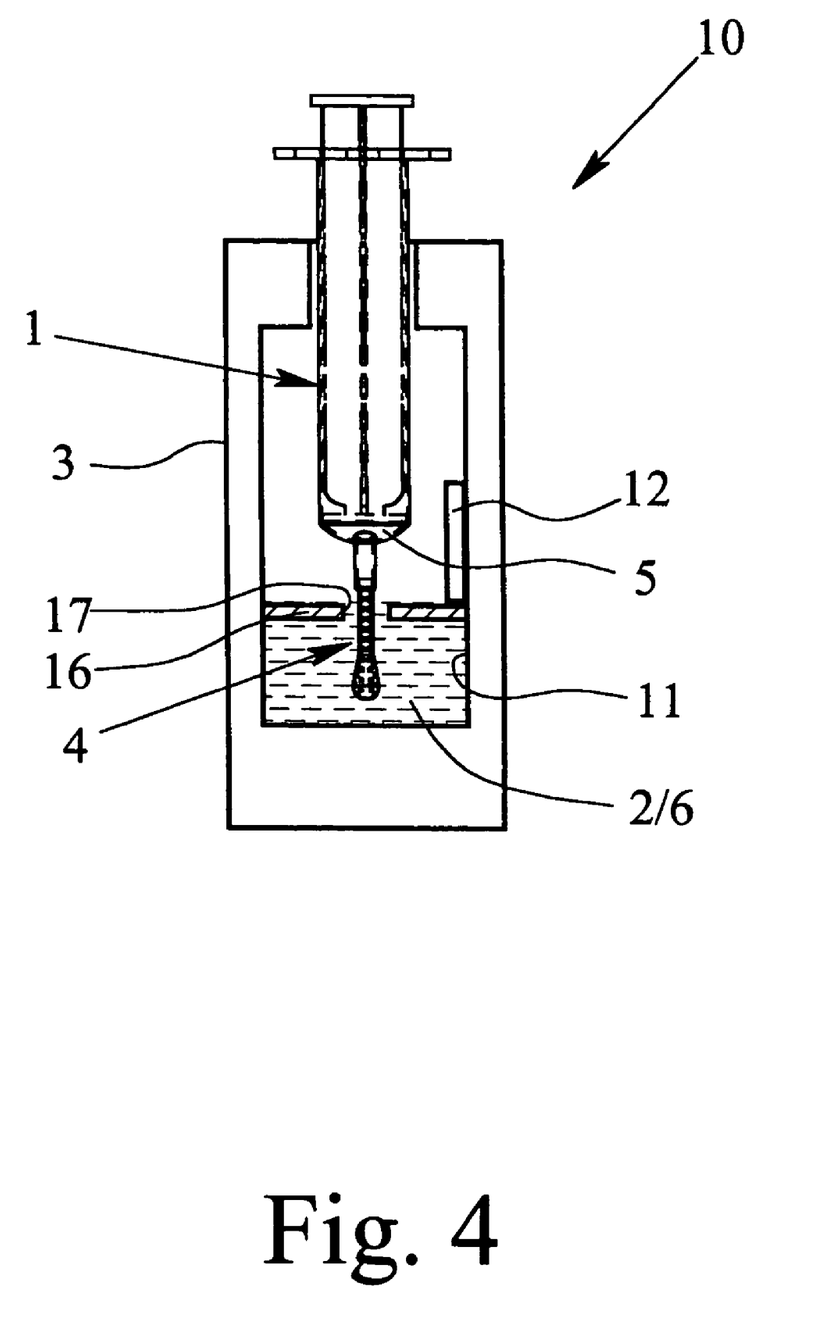
FIG. 4 shows a schematic of a second embodiment of a system in accordance with the invention with a sampling means in accordance with the invention.

The sampling means 1 is intended only for temporarily taking up especially a certain amount of sample liquid 2 and for subsequent delivery of the sample liquid 2, especially to a testing means 3, as shown in FIG. 4.

As FIG. 1 shows, the sampling means 1 has a take-up means 4 for the sample liquid 2. The sampling means 1 also has a reservoir 5 for a dilution liquid 6 (as the term is defined above) and is made such that the sample liquid 2 which has been taken up by the sampling means 1 and by its take-up means 4 and the dilution liquid 6 can be delivered in succession or at the same time, especially by a single actuation of the sampling means 1. To do this, in the initial state, therefore, before sampling, the dilution liquid 6 is already in the reservoir 5.

The take-up means 4 can be filled with the sample liquid 2 preferably independently of the reservoir 5. The take-up means 4 can preferably be filled automatically with the sample liquid 2.

According to one especially preferred configuration, the take-up means 4 has a capillary 7 for taking up the sample liquid 2. The capillary 7 is preferably provided with a ventilation opening 8—for example, at half the length of the capillary 7—with a cross section which is preferably smaller than the cross section of the capillary 7. The ventilation opening 8 branches off laterally from the capillary 7, and therefore constitutes a side opening or hole through the wall of the capillary 7. The capillary 7 and the ventilation opening 8 are shown only schematically in FIG. 1.

Alternatively or in addition, the ventilation opening 8 can also be located on the front surface and/or there can be several ventilation openings 8.

Between the take-up means 4 and the reservoir 5, ventilation is preferably formed, especially to enable the preferred automatic take-up of sample liquid 2.

Upon contact with the sample liquid 2, in the illustrated example, the capillary 7 is automatically filled with the sample liquid 2 up to the level of the ventilation opening 8.

Then, the sample liquid 2 which has been taken up by the sampling means 1 and the take-up means 4 can be discharged with or through the dilution liquid 6. To do this, the sampling means 1 has a preferably manually actuated pump means 9 which, in this example, is formed by a piston, plunger or the like which can be pushed down. In particular, the sampling means 1 with the take-up means 4, the reservoir 5 and the pump means 9 forms a preferably mobile or portable unit which can be manually handled, preferably essentially in a syringe form.

Preferably, the sampling means 1 is made such that the dilution liquid 6 is taken up and integrated in such a manner that it cannot run out or and it can be stored. The protection against running out—for example, a membrane or the like—is then cancelled by actuating the pump means 9—for example, by the pressure of the dilution liquid 6.

Figure 2:
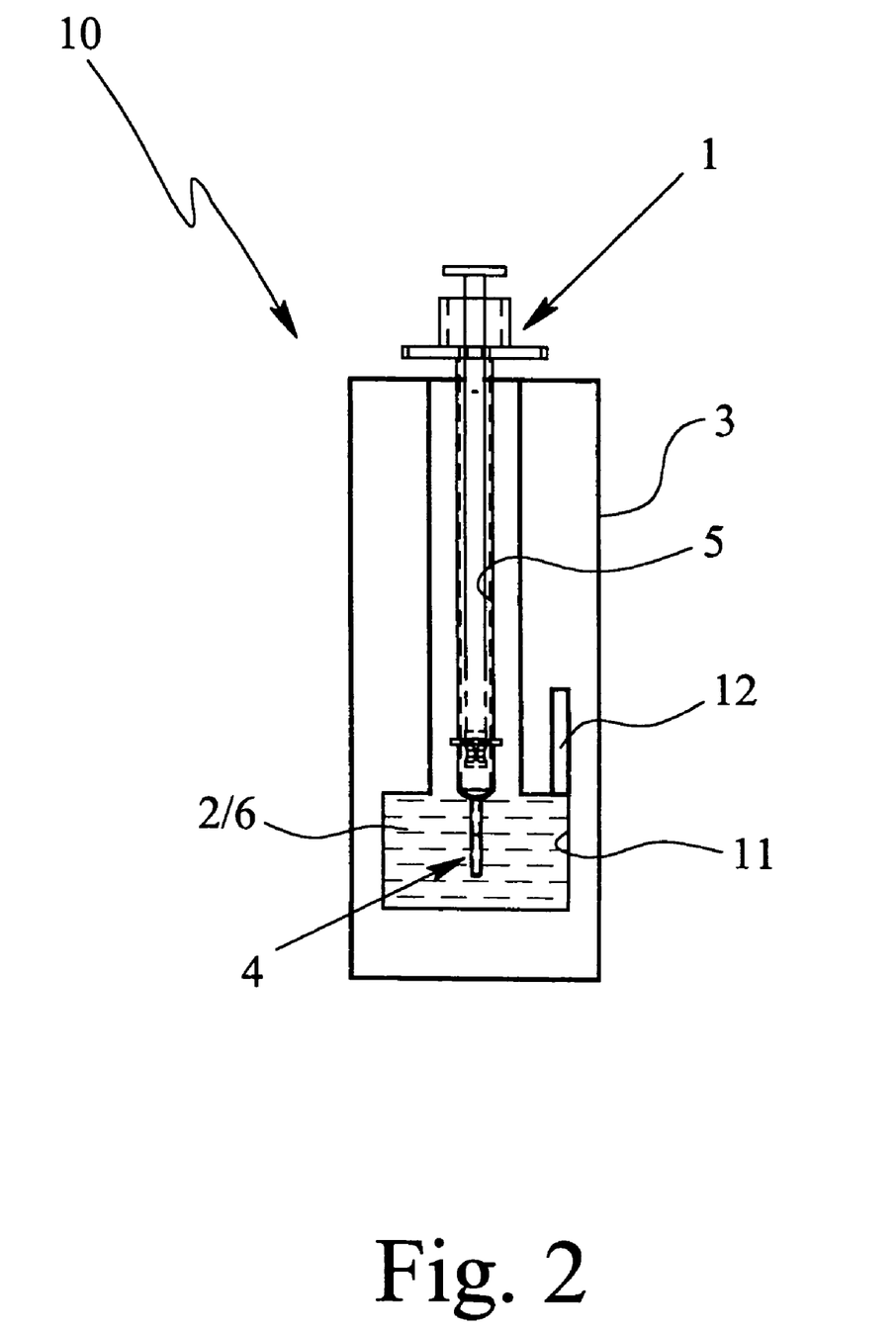
FIG. 2 is a schematic section of a system according to a first embodiment of the invention using the sampling means as shown in FIG. 1 and a testing means into which the sampling means is inserted.

After inserting the sampling means 1 into the testing means 3, as is shown in FIG. 2, the sample liquid 2 which has been taken up by the sampling means 1 is discharged again by the take-up means 4 with the dilution liquid 6 for delivery of the sample liquid 2 and the dilution liquid 6 being flushed by actuating the pump means 9. Thus, the sample liquid 2 which has been taken up beforehand is washed out.

The sampling means 1 of the invention and the testing means 3 together form the system 10 of the invention for testing the sample liquid 2. This is explained in detail below.

The testing means 3 in the illustrated embodiment has a take-up chamber 11 for holding the sample liquid 2 and the dilution liquid 6. When the pump means 9 is actuated, in the illustrated example, first the sample liquid 2 which is in the capillary 7 is expelled by the dilution liquid 6 which is flowing afterwards and is discharged into the underlying take-up chamber 11 which surrounds especially the free end of the take-up means 4. The dilution liquid 6 which is flowing afterwards washes or flushes through the take-up means 4, especially its capillary 7. If the dilution liquid 6 emerges through the ventilation opening 8, this is not disruptive, since this dilution liquid 6 is also taken up by the correspondingly configured take-up chamber 11.

The dilution liquid 6 which continues to flow afterwards in the take-up chamber 11 leads to direct mixing and/or reaction with the sample liquid 2 and thus to the desired dilution and/or reaction of the sample liquid 2 which is necessary for subsequent testing.

The inserted end of the take-up means 4, after locking or fixing the sampling means 1 in the testing means 3 in the vertical or axial direction, is located preferably roughly centrally within the take-up chamber 11. In this way, the sample liquid 2, during the flushing or discharge process, first strikes the bottom of the take-up chamber 11 and swirls there.

To optimize the mixing of the sample liquid 2 with the dilution liquid 6, the take-up chamber 11 can have a shape which promotes mixing—for example, for producing turbulent flows and swirls—and/or a static mixer or the like, for example, on the bottom.

Alternatively, the sampling means 1 can also be made such that the sample liquid 2 can be mixed with the dilution liquid 6 in the sampling means 1. However, preferably the above described mixing is provided only during or after the delivery from the sampling means 1.

In order to enable dilution which is sufficient as necessary, the take-up volume of the reservoir 5 for the dilution liquid 6 can be greater than the take-up volume of the take-up means 4 for the sample liquid 2, at least by a factor of 2, 5 or 10, preferably 100, especially 1000. Such high dilution is important, for example, in the determination of the HbA1c value. However, there are also applications in which the transfer of the sample liquid 2 and/or the mixing and optionally reaction of the sample liquid 2 with reagents in the dilution liquid 6 is what is important; therefore dilution is not important.

To test or analyze the diluted or reacted sample liquid 2 the testing means 3 has the analysis means 12 which is shown schematically in FIG. 2.

Preferably the testing means 3 is made such that analysis can be carried out only during or after reaching a certain fill amount, especially a fill level, in the take-up chamber 11 by the sample liquid 2 and the dilution liquid 6 and/or only after a certain time, especially only then can the diluted sample liquid 2 be supplied to the analysis means 12. This is preferably achieved in that the analysis means 12 is located at a corresponding height relative to the take-up chamber 11, so that analysis is started for example only after wetting, and/or the analysis means 12 is separated from the take-up chamber 11 by a surge wall or the like which must be overcome by the sample liquid 2. This ensures that only a relatively diluted sample which has therefore been prepared for analysis can be analyzed.

The analysis means 12 is made preferably for microfluidic diagnostics. Accordingly, the diluted sample liquid 2 can be supplied preferably automatically, especially by capillary forces, to the analysis means 12 and/or can be conveyed within it for analysis.

The analysis means 12 has components or reagents which are necessary for diagnostics or testing. For example the analysis means 12 has a structured sample carrier and/or a reagent test strip. Relatively or additionally the analysis means 12 can also have or use, for example, a dried up reagent or the like which has been applied directly to the wall of the testing means 3.

In particular, the analysis means 12 has the reagents which are necessary for analysis of the sample liquid 2 and can moreover contain the fluid structures necessary for the execution of analysis, for example, for metering and mixing.

The analysis means 12, in the simplest case, is an unstructured area on the wall, for example, of the testing means 3, especially in the take-up chamber 11 on which the reagent which is necessary for analysis of the sample liquid 2 is immobilized, especially dried up. Furthermore, a certain wall area can be structured, for example, by channels, cavities and the like.

The analysis means 12 can also be a reagent carrier which is placed, especially inserted in the testing means 3, for example, an unstructured film or a microstructured channel plate, especially of plastic, glass, silicon, or a filter test strip, especially of nitrocellulose, paper, cloth or filter paper, a lateral flow test strip or the like.

Figure 3:
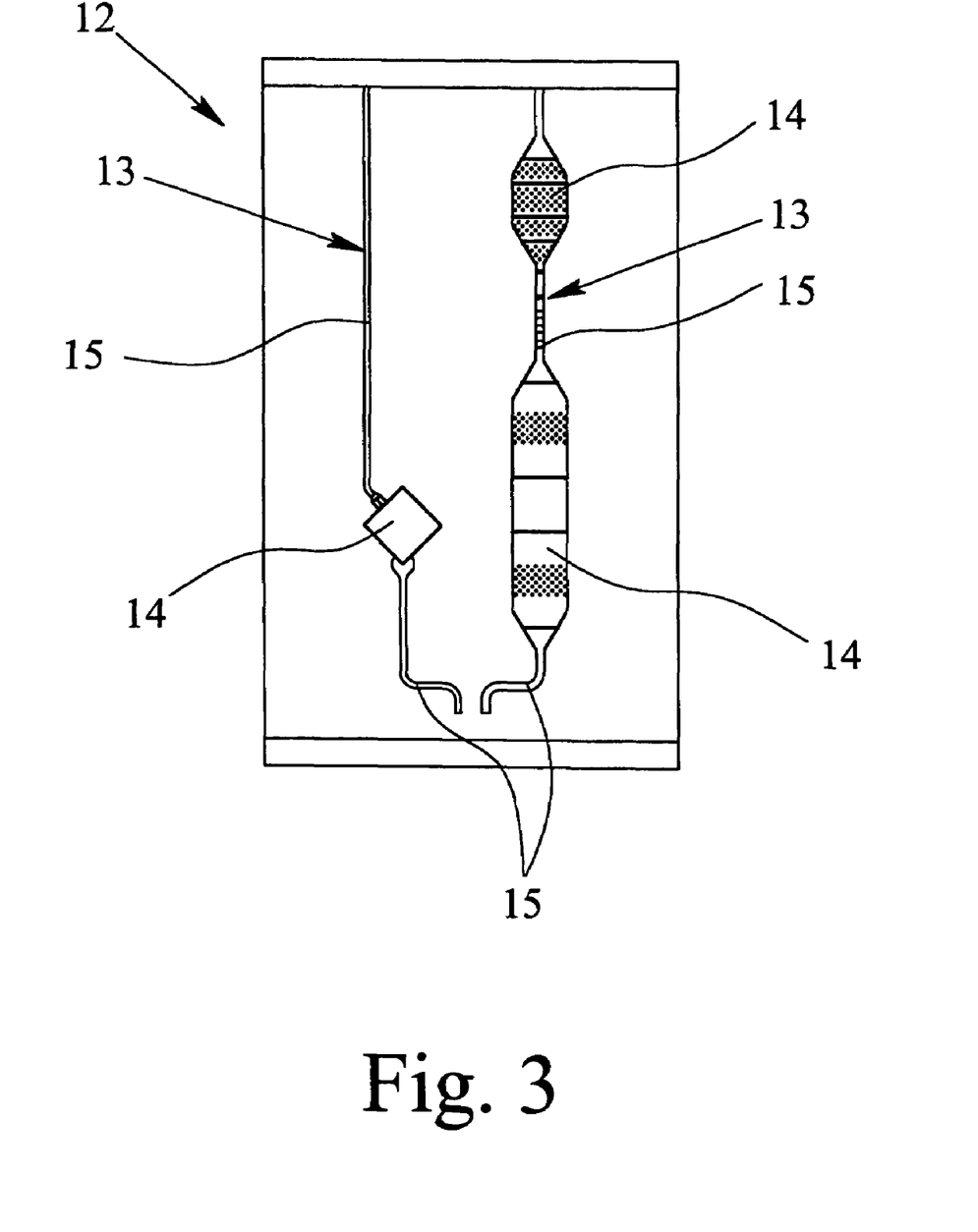
FIG. 3 is a schematic of an analysis means of the testing means as shown in FIG. 2.

In the illustrated example shown in FIG. 3, the analysis means 12 is formed especially by a so-called microtiter plate or a so-called analysis chip or the like.

In the first embodiment, the analysis means 12 is made preferably for the testing of blood as the sample liquid 2, preferably for determining a blood value, especially the so-called HbA1c value. Determining the HbA1c value is especially a quantitative test, the dilution ratio in particular being fixed.

FIG. 3 shows by way of example one possible structure of the analysis means 12. The analysis means 12 here has two reaction branches 13 with chambers 14 and channels 15. By corresponding reagents in the chambers 14 and reactions which proceed in a dedicated manner the desired test, especially the determination of the desired value or the desired ratio, can take place.

Regarding the first embodiment, it is noted that the sampling means 1 is made preferably elongated and/or cylindrical, optionally in the manner of a syringe, in order to facilitate intuitively correct handling.

The testing means 3 preferably has a recess or opening which is matched to the sampling means 1 so that the sampling means 1 can be inserted intuitively correctly into the testing means 3. Preferably, the inserted sampling means 1 closes the recess or the opening of the testing means 3 at least for the most part, in order to be able to avoid unwanted contamination and thus errors in testing.

In the chambers 14, after the (diluted) sample liquid 2 flows in, measurements, manipulations, tests or reactions, for example, for biological, especially microbiological, or chemical diagnostics, can take place, especially with or by reagents which are not shown and which are located in the chambers 14 or by other actions. Preferably, the reagents are placed in the chambers 14 beforehand. In order to be able to carry out or track the tests or reactions, preferably optically—for example, by transmission, fluorescence or turbidity measurements—the analysis means 12 is preferably produced from a relatively transparent material or is made transparent preferably at least in areas. Alternatively or additionally the measurements or tests can however also take place electrically or in some other way.

The volume of the dilution liquid 6 and the sample liquid 2 which has been metered or taken up with the sampling means 1 or by the take-up means 4 together is laid out such that especially only after complete transfer of the two liquids 2, 6 into the testing means 3 is a fill quantity or a fill level reached in the take-up chamber 11 at which the diluted sample liquid 2 enters into contact with the lower area of the analysis means 12 and can wet it. This wetting first starts the actual analysis or other test.

Depending on the application, the sampling means 1 can also contain a larger volume of dilution liquid 6 than absolutely essential. Then, the testing means 3 is preferably made such that when a certain fill amount or fill level is reached in the take-up chamber 11, testing takes place by the analysis means 12. At this time, then a certain dilution ratio has been established which is fixed depending on the accuracy of fixing the volume of the sample liquid 2 which has been taken up by the take-up means 4.

In the case of the first embodiment, the take-up volume of the sample liquid 2 is determined relatively accurately by the capillary 7 so that accordingly the desired dilution ratio can be achieved with the corresponding dimensioning of the take-up chamber 11 and especially the arrangement of the analysis means 12.

Possibly excess dilution liquid 6 then leads to more extensive dilution which preferably no longer significantly influences the test or analysis. Rather the testing means 3 is preferably made such that this excess dilution liquid 6 together with the sample liquid 2 which has been further diluted can flow out of the take-up chamber 11 into a preferably provided overflow space or the like. This prevents the excess liquids 2, 6 from flowing out of the testing means 3 after reaching the desired fill amount or fill level.

Figure 5:
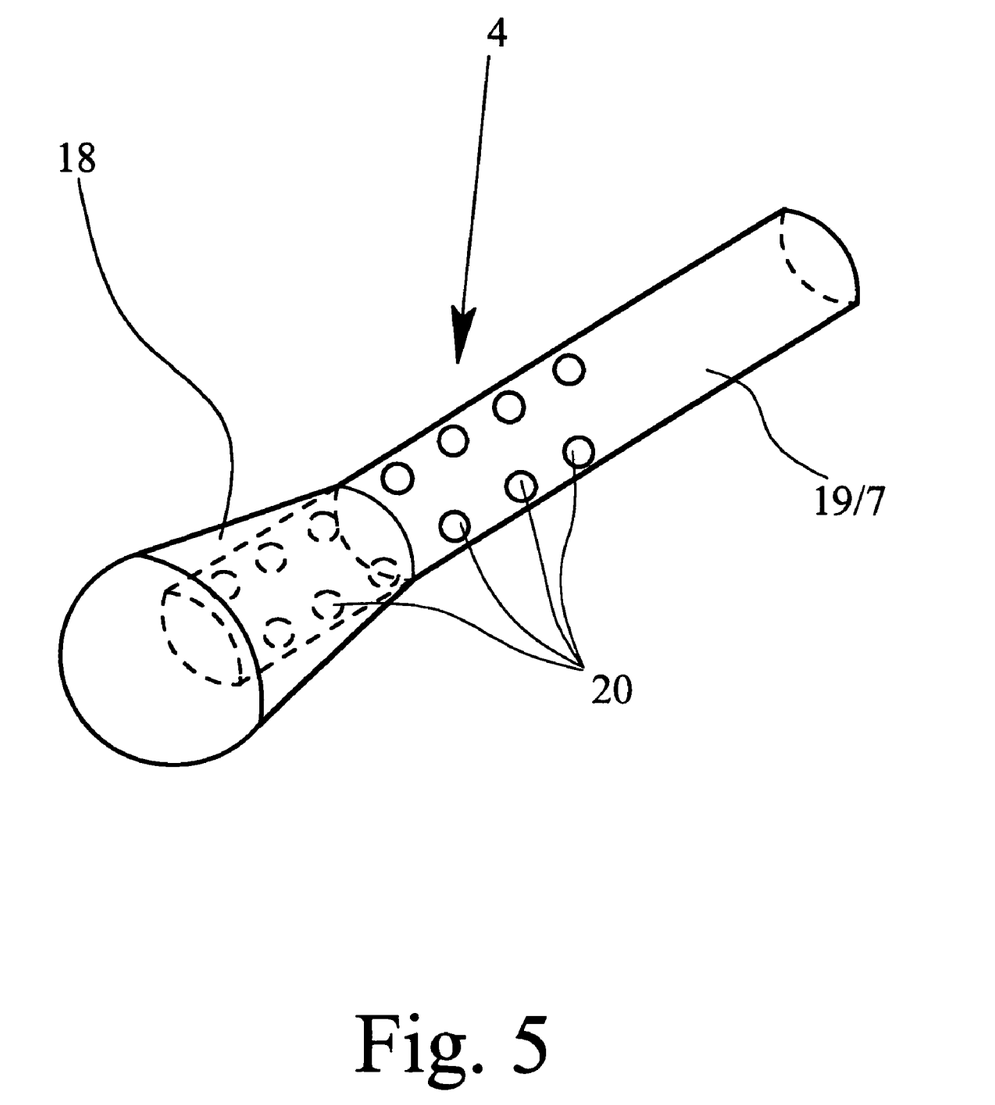
FIG. 5 shows a schematic of a preferred take-up means of the sampling means as shown in FIG. 1 for taking up the sample liquid.

A second embodiment of the sampling means 1 of the invention and of the system in accordance with the invention for testing the sample liquid 2 is explained below using FIGS. 4 to 6; however, only major differences from the first embodiment are emphasized. The statements on the first embodiment therefore otherwise apply accordingly.

The system 10 of the invention according to the second embodiment is shown schematically in FIG. 4. In contrast to the first embodiment, the take-up chamber 11 of the testing means 3 is not bounded or formed by an additional side wall, but is formed directly by the bottom part of the housing of the testing means 3.

Furthermore the take-up chamber 11 in the illustrated embodiment is provided with a covering or surge wall 16 which preferably has an opening 17 through which the sampling means 1, especially its take-up means 4, can be inserted into the take-up chamber 11. In this way, it can be ensured that none of the liquids 2, 6 directly reach the analysis means 12 or is sprayed onto it when the sample liquid 2 is washed out of the take-up means 4 by the dilution liquid 6, but that first only the take-up chamber 11 must be filled, by which first of all the desired dilution, and optionally continuing dissolution, mixing and/or reaction of the sample liquid 2 with the dilution liquid 6, are achieved.

Only after filling the take-up chamber 11 can the diluted sample liquid 2 pass through the opening 17 or through a separate opening (not shown) through the surge wall 16 or can overcome it and travel to the analysis means 12 for subsequent testing.

As in the first embodiment, testing proceeds preferably automatically in turn. In particular, also as in the first embodiment, no shaking or separate step for mixing or diluting the sample liquid 2 with the dilution liquid 6 is necessary. Rather, it is sufficient to deliver the sample liquid 2 and the dilution liquid 6 from the sampling means 1 to the testing means 3 or into its take-up chamber 11 especially by the pump means 9.

In the second embodiment, the sampling means 1 is made especially for taking up saliva or other fluid of the human or an animal body, such as urine, as the sample liquid 2. In particular, for this purpose, the take-up means 4 has a take-up body 18 for the sample liquid 2.

The take-up body 18 is preferably made porous, to have a suction or absorption capacity, fleece-like, wadding-like and/or honeycomb-like and is attached to a hollow and/or perforated holding element 19 which is formed in particular by a capillary 7 which is closed on one side and which is preferably made of plastic, with the corresponding side openings 20 or perforations. In particular, the take-up body 18 surrounds the holding element 19 at least in one end area.

The capillary 7 can, if necessary, also be opened on both ends. Likewise, the use of several through openings 20 increases the efficiency when the sample liquid 2 is being washed out or discharged from the take-up body 18 by the dilution liquid 6.

The take-up body 18 with its preferably absorbent material is used for actually taking up the sample liquid 2, especially saliva, perspiration, tears or the like.

However, alternatively or in addition, a sample liquid 2 can also be taken up by the holding element 19 which is hollow in the illustrated embodiment.

By pressing the piston 9 down, the dilution liquid 6 is pressed through the holding element 19 and the through openings 20 into the take-up body 18, by which it or the sample liquid 2 which is located in it is washed out for transfer to the testing means 3.

Figure 6:
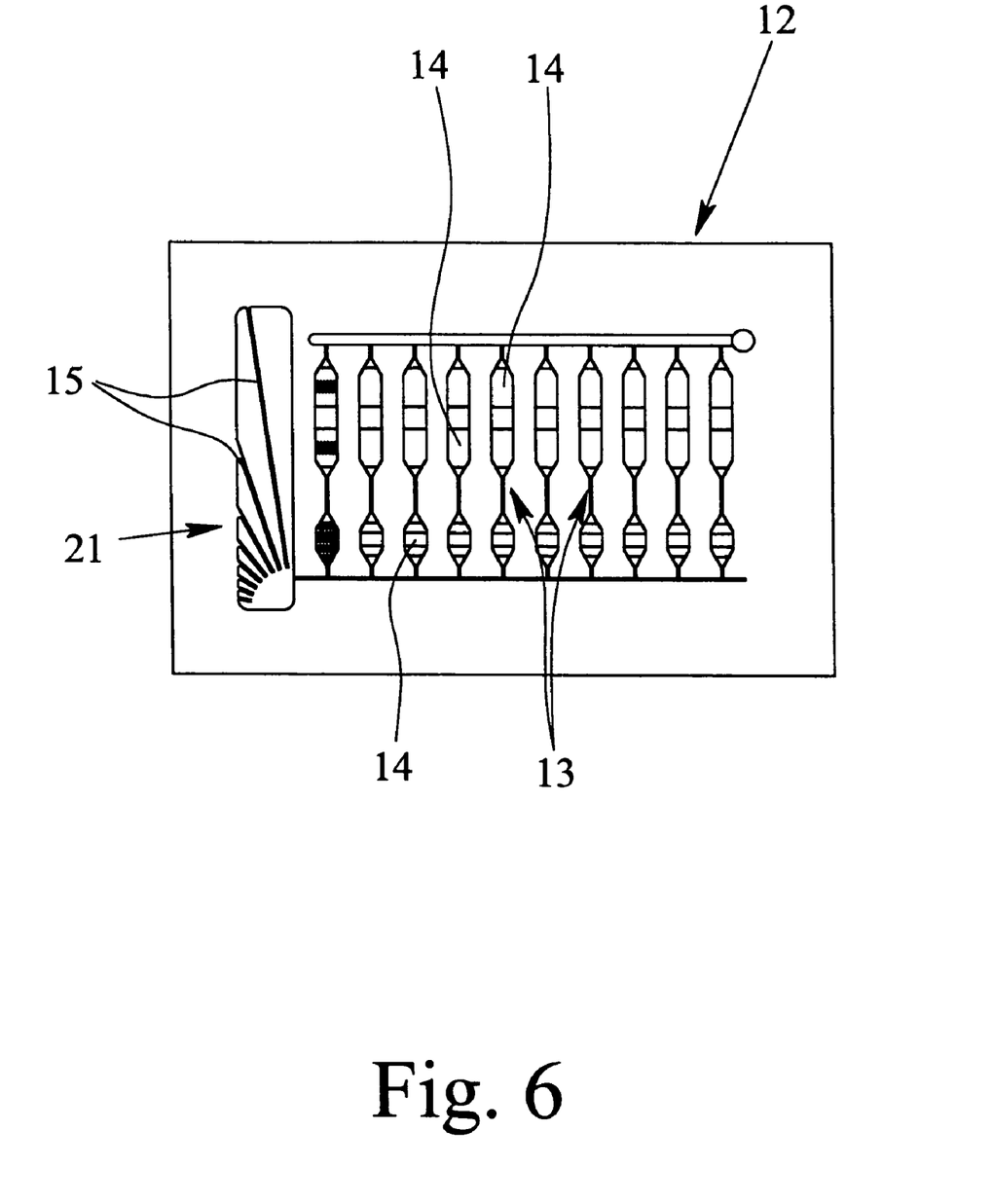
FIG. 6 shows a schematic of an analysis means of the system as shown in FIG. 4.

FIG. 6 schematically shows a preferred structure of the analysis means 12 according to the second embodiment. Compared to the first embodiment, the analysis means 12 of this embodiment, preferably, has more reaction chambers and detection or testing chambers 14. In addition, the analysis means 12 has an enlarged, especially widened take-up area 21 with a host of (capillary) channels 15 in order to be able to take up the diluted sample liquid 2 more rapidly and/or in a larger amount.

According to a preferred version, the analysis means 12 is made for testing saliva, especially for determination of alcohol, HIV, medications or drugs in the saliva.

According to another version, the analysis means 12 is made additionally or alternatively for testing of urine, especially for determining microalbumin and/or creatine.

Figure 7:
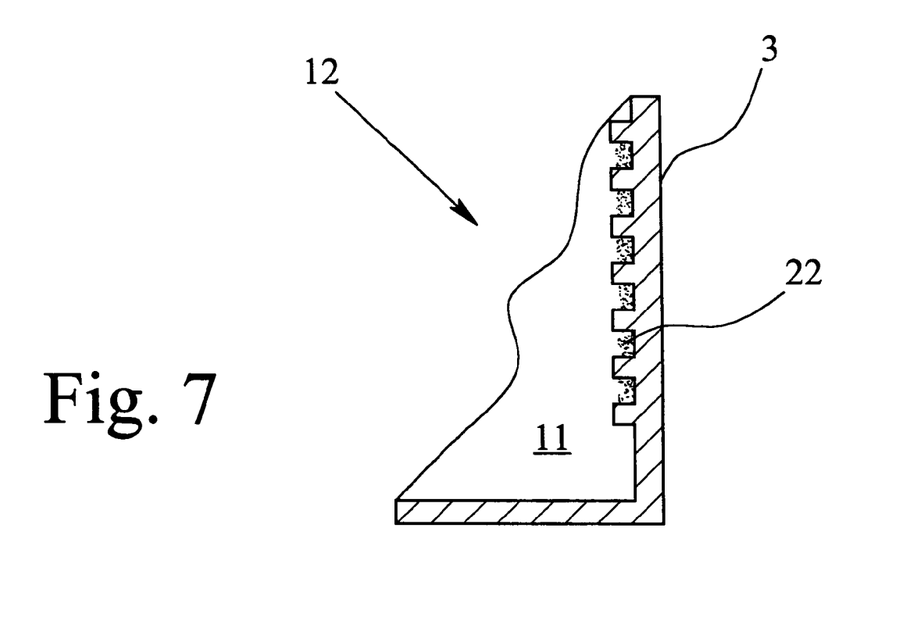
FIG. 7 schematically shows a section of an analysis means according to a third embodiment.

FIG. 7 shows in a highly schematic portion of the analysis means 12 according to a third embodiment. Here, an inner wall of the testing means 3 or the take-up chamber 11 is provided with the reagent 22 of the analysis means 12 which, after adding the diluted sample liquid 2, is partially dissolved by it and can react with it for testing or diagnostics. For example, the reagent 22 is dried directly on the inner wall or is attached in some other way.

In the FIG. 7 embodiment, the inside wall—at least in areas—is preferably provided with a certain surface texture and/or is microstructured in order to increase the wettability and/or to take up the reagent 22. In particular, the reagent 22 is dried up in this microstructure.

When the sample liquid 2, as it is added to the take-up chamber 11, due to further addition of dilution liquid 6 reaches the height of the analysis means 12 and wets it, the reagent 22 can be partially dissolved and the desired reaction, test or the like can take place.

Figure 8:
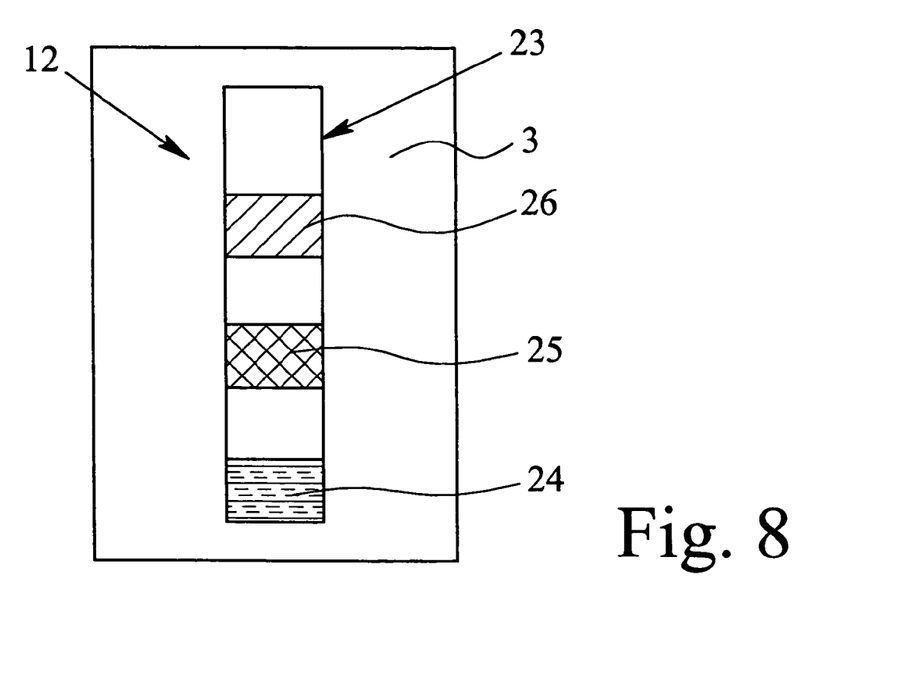
FIG. 8 schematically shows an analysis means according to a fourth embodiment.

FIG. 8 shows a fourth embodiment of an analysis means 12 which has a test strip 23 with dried-up and/or immobilized reagents—in this embodiment, three areas 24, 25, 26 with different reagents are illustrated.

After reaching a certain fill level in the take-up chamber 11, the lower part of the test strip 23 is wetted by the diluted sample liquid 2 which is then transported as a result of capillary forces through the test strip 23 and reacts there with the reagents. In particular, a color change takes place here, depending on the reaction with the reagents.

The test strip 23 can, for example, have several test fields or areas 24, 25, 26 for different parameters which are to be tested, as is conventional in urinalysis.

If necessary, in the take-up chamber 11, a host of test strips 23, optionally also different ones, can be used.

According to one especially preferred version, the analysis means 12 and the test strip 23 can be interchangeably and/or as necessary inserted into the testing means 3. This enables especially versatile use of the testing means 3 and thus of the system 10 of the invention.

Preferably, the testing means 3 and the wall of the take-up chamber 11 have suitable holding means (not shown) for optionally detachable or interchangeable holding of the analysis means 12, especially of the test strip 23. For example, the test strip 23 can be inserted into a corresponding guide, groove or the like.

If necessary, the test strip 23 can be constructed in a manner suitable for so-called immunochromatography and can form a so-called sandwich immuno-array. In particular, the test strip 23 then has a blood separation section, an area which especially absorbs an antibody-latex conjugate, a nitrocellulose membrane with a test belt and a control belt and/or a downstream absorbing area. However, this version is not shown.

Figure 9:
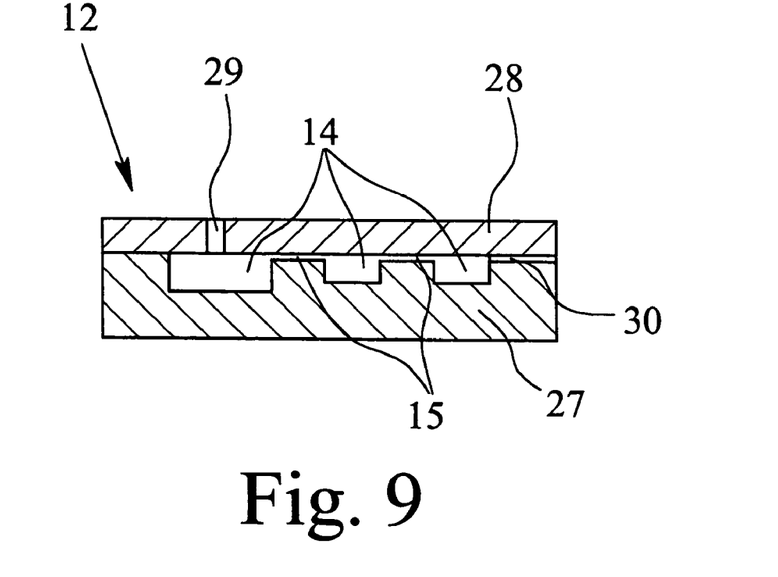
FIG. 9 is sectional view of an analysis means according to a fifth embodiment.
Figure 10:
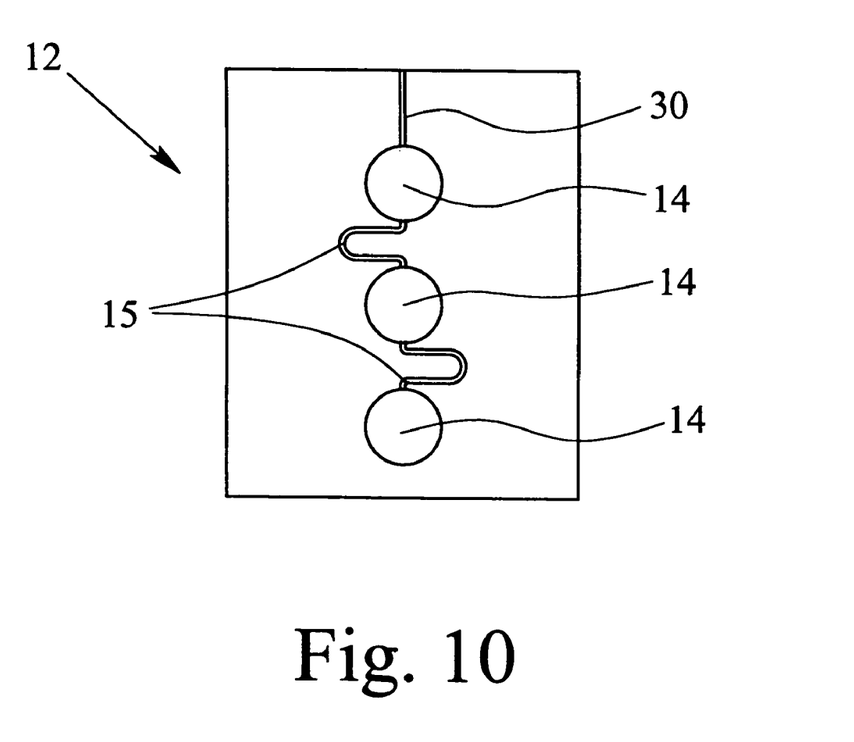
FIG. 10 is a plan view of the analysis means as shown in FIG. 9.

FIG. 9 shows, in a schematic cross section, the analysis means 12 according to a fifth embodiment. FIG. 10 shows a plan view of this analysis means 12.

In a plate 27, cavities are formed for holding the diluted sample liquid 2. The cavities, like the chambers 14 and 15, are formed especially in a flat side of the plate 27 and are covered by a preferably film-like covering 28. Accordingly, the cavities form a more or less closed capillary system.

In the illustrated example, the analysis means 12 has a take-up opening 29 which is formed especially in the covering 28 for taking up the diluted sample liquid 2, preferably, when the diluted sample liquid 2 reaches the take-up opening 29 based on the corresponding fill level in the take-up chamber 11 of the testing means 3.

The diluted sample liquid 2 can then flow into the first chamber 14 and especially as a result of the corresponding execution of the chambers 14, channels 15 and the transitions which lie in between—is transported by capillary forces through the capillary system in order to fill especially the other chambers 14 and to react there with the optionally dried-up reagents which have been added beforehand in order to enable the desired diagnostics or testing.

The analysis means 12 has a ventilation opening 30 so that when the capillary system is filled the air which has been displaced by the penetrating sample liquid 2 can escape from the capillary system.

Preferably, in turn, the analysis means 12 is made, at least in areas, transparent enough to enable especially visual detection and testing.

The plate 27 is preferably microstructured and can be produced, for example, from plastic, glass, ceramic, silicon, silicone, or the like. However, if necessary, the plate 27 can also be a film or other suitable carrier. The corresponding also applies to the covering 28. If necessary, the covering 28 can also only partially cover the plate 27.

The sampling means 1 of the invention according to the described embodiments is preferably made portable. The testing means 3 is preferably likewise made portable. Accordingly a mobile, especially portable system 10 for testing the sample liquid 2 results.

The sampling means 1 in accordance with the invention and the system 10 of the invention can be used in a very versatile manner. In many immunologic or biochemical tests at the point of care or in the self-testing sector, it is necessary to greatly dilute the sample liquid 2. The dilution must be very uniform and must be quantitatively determined. In particular, when using blood samples, the object is to use sample volumes as small as possible. Volumes in the range between 1 μl and 5 μl are desirable. The dilution factors are typically 1:50 to 1:300. The sampling means 1 of the invention and the system 10 according to the invention are ideally suited for this purpose.

The sample liquid 2 can be removed easily, promptly and especially hygienically. Metering is ensured in this take-up and removal step.

The removed sample liquid 2 is then placed in one step in the testing means 3 where further processing and analysis or testing can be started. When the sample liquid 2 is added in this way, the desired dilution takes place. Intermediate steps for sample preparation outside of the system 10 of the invention are not necessary. In particular, the sampling and the execution of analysis and of tests can be carried out by individuals who have not been trained in medicine.

One special advantage of the approach of the invention is that the sampling means 1 combines both removal of the sample liquid 2 and also the storage and thus preparation of the dilution liquid 6, especially of a dilution buffer or the line, in one device.

What is claimed is:

1. Portable sampling device for taking up and delivery of a sample liquid comprising:
   a take-up means for taking up the sample liquid,
   an reservoir for a dilution liquid that is integrated with the take-up means, and
   a manually actuated pump means for delivering both the sample liquid and the dilution liquid; and
   wherein said take-up means for the sample liquid is taken up is also a discharge means through which the sample liquid and the dilution are discharged together;
   wherein the take-up means for the sample liquid and the reservoir for the dilution liquid are arranged relative to each other and said pump means so that a defined amount of said liquids is delivered by a single actuation of the pump means; and
   wherein the take-up means has a capillary for drawing in the sample liquid.

2. Portable sampling device as claimed in claim 1, wherein the sample liquid is mixed with the dilution liquid during delivery.

3. Portable sampling device as claimed in claim 1, wherein the reservoir has a take-up volume that is larger than a take-up volume of the take-up means by at least a factor of 10.

4. Portable sampling device as claimed in claim 1, wherein the reservoir has a take-up volume that is larger than a take-up volume of the take-up means by at least a factor of 1000.

5. Portable sampling device as claimed in claim 1, wherein the take-up means is fillable with the sample liquid independently of the reservoir- 6. Portable sampling device as claimed in claim 1, wherein the take-up means is automatically fillable with the sample liquid.

7. Portable sampling device as claimed in claim 1, wherein the capillary has a ventilation opening.

8. Portable sampling device as claimed in claim 7, wherein the cross section of the ventilation opening is smaller than the cross section of the capillary.

9. Portable sampling device as claimed in claim 7, wherein the ventilation opening branches off laterally from the capillary.

10. Portable sampling device as claimed in claim 1 wherein the take-up means for the sample liquid and the reservoir for the dilution liquid are arranged relative to each other and said pump means so that the sample liquid is discharged from the take-up means by the dilution liquid.

11. Portable sampling device as claimed in claim 10, wherein the take-up means is flushed by the dilution liquid for delivery of the sample liquid and the dilution liquid.

12. Portable sampling device for taking up an and delivery of a sample liquid, comprising:
   a take-up means for taking up the sample liquid,
   an reservoir for a dilution liquid that is integrated with the take-up means, and
   a manually actuated pump means for delivering both the sample liquid and the dilution liquid; and
   wherein said take-up means through which the sample liquid is taken up is also a discharge means through which the sample liquid and the dilution liquid are discharged together;
   wherein the take-up means for the sample liquid and the reservoir for the dilution liquid are arranged relative to each other and said pump means so that a defined amount of said liquids is delivered by a single actuation of the pump means; and
   wherein the take-up means has a take-up body for the sample liquid, and
   wherein the take-up body is made of a porous material to have a suction capacity.

13. Portable sampling means as claimed in claim 12, wherein the porous material comprises at least one of a fleece, wadding and honeycomb material.

14. Portable sampling device as claimed in claim 12, wherein the take-up means is fillable with the sample liquid independently of the reservoir.

15. Portable sampling device as claimed in claim 12, wherein the take-up means is automatically fillable with the sample liquid.

16. Portable sampling device as claimed in claim 12, wherein the take-up means for the sample liquid and the reservoir for the dilution liquid are arranged relative to each other and said pump means so that the sample liquid is discharged from the take-up means by the dilution liquid.

17. Portable sampling device as claimed in claim 16, wherein the take-up means is flushed by the dilution liquid for delivery of the sample liquid and the dilution liquid.

18. Portable sampling device as claimed in claim 12, wherein the sample liquid is mixed with the dilution liquid during delivery.

19. Portable sampling device as claimed in claim 12, wherein the reservoir has a take-up volume that is larger than a take-up volume of the take-up means by at least a factor of 10.

20. Portable sampling device as claimed in claim 12, wherein the reservoir has a take-up volume that is larger than a take-up volume of the take-up means by at least a factor of 1000.

21. Portable sampling device for taking up and delivery of a sample liquid, comprising:
   a take-up means for taking tin the sample liquid,
   an reservoir for a dilution liquid that is integrated with the take-up means, and
   a manually actuated pump means for delivering both the sample liquid and the dilution liquid: and
   wherein said take-up means through which the sample liquid is taken up is also a discharge means through which the sample liquid and the dilution liquid are discharged together;
   wherein the take-up means for the sample liquid and the reservoir for the dilution liquid are arranged relative to each other and said pump means so that a define amount of said liquids is delivered by a single actuation of the pump means; and
   wherein the pump means has a depressible piston.

22. Portable sampling device as claimed in claim 21, wherein the take-up means has a capillary for drawing in the sample liquid.

23. Portable sampling device as claimed in claim 21, wherein the take-up body is made of a porous material to have a suction capacity.

24. Portable sampling device as claimed in claim 21, wherein the take-up means is fillable with the sample liquid independently of the reservoir.

25. Portable sampling device as claimed in claim 21, wherein the take-up means is automatically fillable with the sample liquid.

26. Portable sampling device as claimed in claim 23, wherein the take-up means for the sample liquid and the reservoir for the dilution liquid are arranged relative to each other and said pump means so that the sample liquid is discharged from the take-up means by the dilution liquid.

27. Portable sampling device as claimed in claim 26, wherein the take-up means is flushed by the dilution liquid for delivery of the sample liquid and the dilution liquid.

28. Portable sampling device as claimed in claim 21, wherein the sample liquid is mixed with the dilution liquid during delivery.

29. Portable sampling device as claimed in claim 21, wherein the reservoir has a take-up volume that is larger than a take-up volume of the take-up means by at least a factor of 10.

30. Portable sampling device as claimed in claim 21, wherein the reservoir has a take-up volume that is larger than a take-up volume of the take-up means by at least a factor of 1000.

31. System for testing sample liquid, comprising:
a portable sampling means for taking up and delivering a sample liquid, and
a testing means,
wherein the sampling means has a take-up means for the sample liquid, a reservoir for a dilution liquid, and an manually actuated pump means for delivering both the sample liquid and the dilution liquid to the testing means formed as an integrated unit; wherein the unit has at least one opening through which the sample liquid is taken up and through which the sample liquid and the dilution liquid are discharged together; and
wherein the take-up means for the sample liquid and the reservoir for the dilution liquid are arranged relative to each other and said pump means so that a defined amount of both of said liquids is deliverable by a singe actuation of the pump means.

32. System as claimed in claim 31, wherein the testing means has a take-up chamber for taking up the sample liquid with the dilution liquid.

33. Portable sampling device as claimed in claim 32, wherein the take-up body is attached to a holding element that is at least one of hollow and perforated.

34. System as claimed in claim 32, wherein the testing means has an analysis means.

35. System as claimed in claim 34, wherein the analysis means comprises a microfluidic diagnostic.

36. System as claimed in claim 31, wherein the testing means has an analysis means.

37. System as claimed in claim 36, wherein the analysis means comprises a microfluidic diagnostic.

38. System as claimed in claim 37, wherein the analysis means is positioned for receiving diluted sample liquid when a certain fill level of sample liquid and dilution liquid is reached in the take-up chamber.

39. System as claimed in claim 36, wherein the analysis means is supplied with diluted sample liquid automatically by capillary forces.

40. System as claimed in claim 36, wherein the analysis means comprises at least one of a microtiter plate, an analysis chip and a test strip.

41. System as claimed in claim 40, wherein the analysis means is interchangeable.

42. System as claimed in claim 36, wherein the take-up means has a take-up chamber, and wherein the analysis means comprises a reagent for reaction with components of the sample liquid, said reagent being located directly on a wall of the take-up chamber.

43. System as claimed in claim 36, wherein the analysis means comprises a relatively material which is transparent at least in areas.

44. System as claimed in claim 36, wherein the analysis means is a means for testing of blood and the dilution liquid contains a lysis reagent for analysis of blood cells.

45. System as claimed in claim 36, wherein the analysis means is a means for testing of saliva.

46. System as claimed in claim 36, wherein the analysis means is a means for testing urine.

47. System as claimed in claim 31, wherein at least one of the sampling means and the testing means are nonelectrical.

48. System as claimed in claim 31, wherein the system is portable.

49. System as claimed in claim 31, wherein the testing means has a recess or opening which is matched to the sampling means and wherein the sampling means is sized to essentially close the recess or opening of the testing means when inserted therein.

50. System as claimed in claim 31, wherein means are provided for holding the dilution liquid in the reservoir without the danger of the dilution liquid running out.

51. System as claimed in claim 31, wherein the take-up means is fillable independently of the reservoir.

52. System as claimed in claim 31, wherein the take-up means is automatically fillable with the sample liquid.

53. System as claimed in claim 31, wherein the take-up means has a capillary for taking up the sample liquid.

54. System as claimed in claim 53, wherein the capillary has a ventilation opening.

55. System as claimed in claim 54, wherein the ventilation opening has a cross section that is smaller than the cross section of the capillary and branch off laterally from the capillary.

56. System means as claimed in claim 31, wherein the take-up means has a take-up body for the sample liquid.

57. System means as claimed in claim 56, wherein the take-up body is porous to have a suction capacity.

58. System means as claimed in claim 57, wherein the take-up body comprises at least one of a fleece, a wadding and a honeycomb.

59. System means as claimed in claim 56, wherein the take-up body is attached to a holding element that is at least one of hollow and perforated.

60. System means as claimed in claim 31, wherein the take-up means for the sample liquid and the reservoir for the dilution liquid are arranged relative to each other and said pump means so that the sample liquid is discharged from the take-up means by the dilution liquid.

61. System as claimed in claim 60, wherein the take-up means is flushed by means of the dilution liquid for delivery of the sample liquid and the dilution liquid.

62. System as claimed in claim 31, wherein the sample liquid is mixed with the dilution liquid during delivery.

63. System as claimed in claim 31, wherein the pump means has a depressible piston.

64. System as claimed in claim 31, wherein the take-up volume of the reservoir is larger than the take-up volume of the take-up means at least by a factor of 10.

* * * * *